(12) United States Patent
Frank

(10) Patent No.: US 8,882,800 B2
(45) Date of Patent: Nov. 11, 2014

(54) MEDICAL INSTRUMENT

(75) Inventor: Timothy Graham Frank, Newport-on-Tay Fife (GB)

(73) Assignee: University of Dundee (GB)

(*) Notice: Subject to any disclaimer, the term of this patent is extended or adjusted under 35 U.S.C. 154(b) by 22 days.

(21) Appl. No.: 13/345,556

(22) Filed: Jan. 6, 2012

(65) Prior Publication Data

US 2012/0179197 A1 Jul. 12, 2012

(30) Foreign Application Priority Data

Jan. 6, 2011 (DE) .......................... 10 2011 008 013

(51) Int. Cl.
*A61B 17/00* (2006.01)
*A61B 17/29* (2006.01)
*A61B 17/30* (2006.01)

(52) U.S. Cl.
CPC ......... *A61B 17/29* (2013.01); *A61B 2017/2938* (2013.01); *A61B 2017/2912* (2013.01); *A61B 2017/305* (2013.01)
USPC ............. 606/206; 606/208; 606/209; 81/345; 81/346; 81/347; 81/355

(58) Field of Classification Search
CPC ............. A61B 2017/2938; A61B 2017/00353; A61B 17/2909; A61B 2017/305; A61B 2017/2912; A61B 17/29
USPC ..................... 606/1, 205–209, 250–259, 139; 294/119.1, 115, 87.1; 600/104; 81/345–351
See application file for complete search history.

(56) References Cited

U.S. PATENT DOCUMENTS

| | | | | |
|---|---|---|---|---|
| 4,872,456 A | * | 10/1989 | Hasson | .......................... 606/207 |
| 5,290,308 A | * | 3/1994 | Knight et al. | .................. 606/205 |
| 5,336,238 A | * | 8/1994 | Holmes et al. | ................. 606/208 |

(Continued)

FOREIGN PATENT DOCUMENTS

| | | |
|---|---|---|
| DE | 4336634 A1 | 5/1995 |
| DE | 19632298 A1 | 2/1998 |

(Continued)

OTHER PUBLICATIONS

European Search Report; Application No. EP 11 00 2021; Issued: Mar. 20, 2012; Mailing Date: Mar. 23, 2012; 8 pages.

(Continued)

*Primary Examiner* — Katherine Dowe
*Assistant Examiner* — Sidharth Kapoor
(74) *Attorney, Agent, or Firm* — St. Onge Steward Johnston & Reens LLC

(57) ABSTRACT

A medical instrument with a shank consisting of pivotable jaw parts and a handle, the two jaw parts of the tool are pivotable relative to each other independently via the handle and each of the pivotable jaw parts is actuated via a separate drive. One drive is designed as a grip part mounted pivotably on the handle and is connected to one jaw part via a first push/pull element mounted in an axially displaceable manner in the shank, and the other drive is an adjusting wheel rotatable about a longitudinal axis of the shank and is connected to the other jaw part of the tool via a second push/pull element mounted in an axially displaceable manner in the shank. The push/pull element is designed as a push/pull rod, and the push/pull element which is coupled to the adjusting wheel is designed as a push/pull tube coaxially surrounding the push/pull rod.

9 Claims, 3 Drawing Sheets

(56) References Cited

U.S. PATENT DOCUMENTS

| | | | |
|---|---|---|---|
| 5,348,259 A * | 9/1994 | Blanco et al. | 248/276.1 |
| 5,403,332 A | 4/1995 | Christoudias | |
| 5,674,230 A * | 10/1997 | Tovey et al. | 606/139 |
| 6,506,208 B2 * | 1/2003 | Hunt et al. | 606/205 |
| 6,673,092 B1 * | 1/2004 | Bacher | 606/205 |
| 2006/0074442 A1 * | 4/2006 | Noriega et al. | 606/159 |
| 2006/0161190 A1 * | 7/2006 | Gadberry et al. | 606/174 |
| 2009/0209991 A1 | 8/2009 | Hinchliffe et al. | |

FOREIGN PATENT DOCUMENTS

| | | | |
|---|---|---|---|
| DE | 4307539 B4 | | 8/2005 |
| EP | 0072689 | * | 2/1983 |
| WO | 9814124 A1 | | 4/1998 |

OTHER PUBLICATIONS

German Search Report; Application No. DE 10 2011 008 013.9; Issued: Sep. 14, 2011; 5 pages.

* cited by examiner

MEDICAL INSTRUMENT

CROSS-REFERENCE TO RELATED APPLICATIONS

The present application claims priority of German patent application No. 10 2011 008 013.9 filed on Jan. 6, 2011, the content of which is incorporated herein by reference.

FIELD OF THE INVENTION

The invention relates to a medical instrument with a shank, at the distal end of which a tool consisting of two pivotable jaw parts is arranged, and at the proximal end of which a handle is arranged, wherein the jaw parts of the tool can be pivoted relative to each other independently of each other via the handle and each of the two jaw parts can be actuated via a separate drive arranged on the handle, wherein one drive is designed as a grip part which is mounted pivotably on the handle and is operatively connected to one jaw part of the tool via a first push/pull element mounted in an axially displaceable manner in the shank, and in that the other drive is designed as an adjusting wheel which is rotatable about the longitudinal axis of the shank and is operatively connected to the other jaw part of the tool via a second push/pull element mounted in an axially displaceable manner in the shank.

BACKGROUND OF THE INVENTION

Medical instruments of this type are frequently used in practice as cutting, punching, grasping and/or holding tools.

A medical instrument of the type in question is disclosed for example, in U.S. Pat. No. 4,872,456 A.

A further medical instrument is disclosed in DE 43 07 539 B4. In these known medical instruments with a tool tip having two pivotable jaw parts, the jaw parts are coupled to an actuating element in such a manner that the jaw parts can always be pivoted in pairs and to the same extent in relation to one another. Although this configuration has been thoroughly tried and tested in practice, flexible and secure grasping and holding of differently shaped objects using said jaw parts is possible only to a limited extent.

SUMMARY OF THE INVENTION

In the light thereof, the problem addressed by the invention is that of providing a medical instrument which is of the type mentioned at the beginning, and which can be used flexibly and ensures a consistently secure grip of the object grasped with the jaw parts.

According to the invention, the solution to this problem is characterized in that the push/pull element which is coupled to the pivotable grip part is designed as a push/pull rod, and in that the push/pull element which is coupled to the adjusting wheel is designed as a push/pull tube coaxially surrounding the push/pull rod.

The embodiment in the form of a push/pull rod and push/pull tube ensures a substantially play-free transmission of force from the driving elements to the respective jaw parts.

The capability of the jaw parts to pivot separately to each other makes it possible to individually adapt the grasping and holding of an object to be gripped by the jaw parts to the object, by adapting the position of the jaw parts to each other, in order to be able to securely place said object between the jaw parts. The separate design of the drives for each jaw part permits individual adaptation of the drives to the requirements imposed on the associated jaw part.

In order to further improve the possibility of use and the flexibility of the instrument according to the invention, it is proposed, with a practical embodiment of the invention, that the jaw parts of the tool can be bent in relation to the longitudinal axis of the instrument. Said bendability makes it possible for the medical instrument to remain in the axial alignment thereof, for example in a trocar sleeve, even if a laterally offset object is to be grasped.

In order to ensure that the insufflation gas cannot escape via the push/pull elements, the push/pull rod and the push/pull tube are mounted in a fluid-proof manner in the handle via sealing elements, in particular O rings.

According to the invention, the rotational movement of the adjusting wheel is converted into the axial movement of the push/pull rod via a helical guide track and a control pin engaging in the guide track, wherein, advantageously, the control pin is fixedly connected to the push/pull tube and the helical guide track is formed in the adjusting wheel or in a sleeve which can be fixed in the adjusting wheel.

Furthermore, it is proposed by the invention that the guide pin is mounted in a manner such that is guided in a longitudinal slot formed in the handle, in order to prevent rotation of the push/pull tube.

According to a second practical embodiment relating to the design according to the invention of the drives, it is proposed that the two drives are designed as levers which are mounted pivotably on the handle, each lever being operatively connected to a respective jaw part of the tool via a respective push/pull element.

With regard to the design of the push/pull elements for actuation of the jaw parts of the tool, it is proposed in this embodiment according to the invention that the two push/pull elements are designed as push/pull rods which are mounted in an axially displaceable manner parallel to each other in the shank.

Finally, it is proposed by the invention that an empty tube which extends as far as the tool and is intended for receiving a medical instrument or a medical aid, such as, for example, a catheter, is additionally arranged in the shank and in the handle.

BRIEF DESCRIPTION OF THE DRAWINGS

Further features and advantages of the invention emerge with reference to the associated drawings, in which two exemplary embodiments of a medical instrument according to the invention are illustrated only by way of example without restricting the invention to these exemplary embodiments. In the drawings.

DETAILED DESCRIPTION OF THE INVENTION

Figure 1:
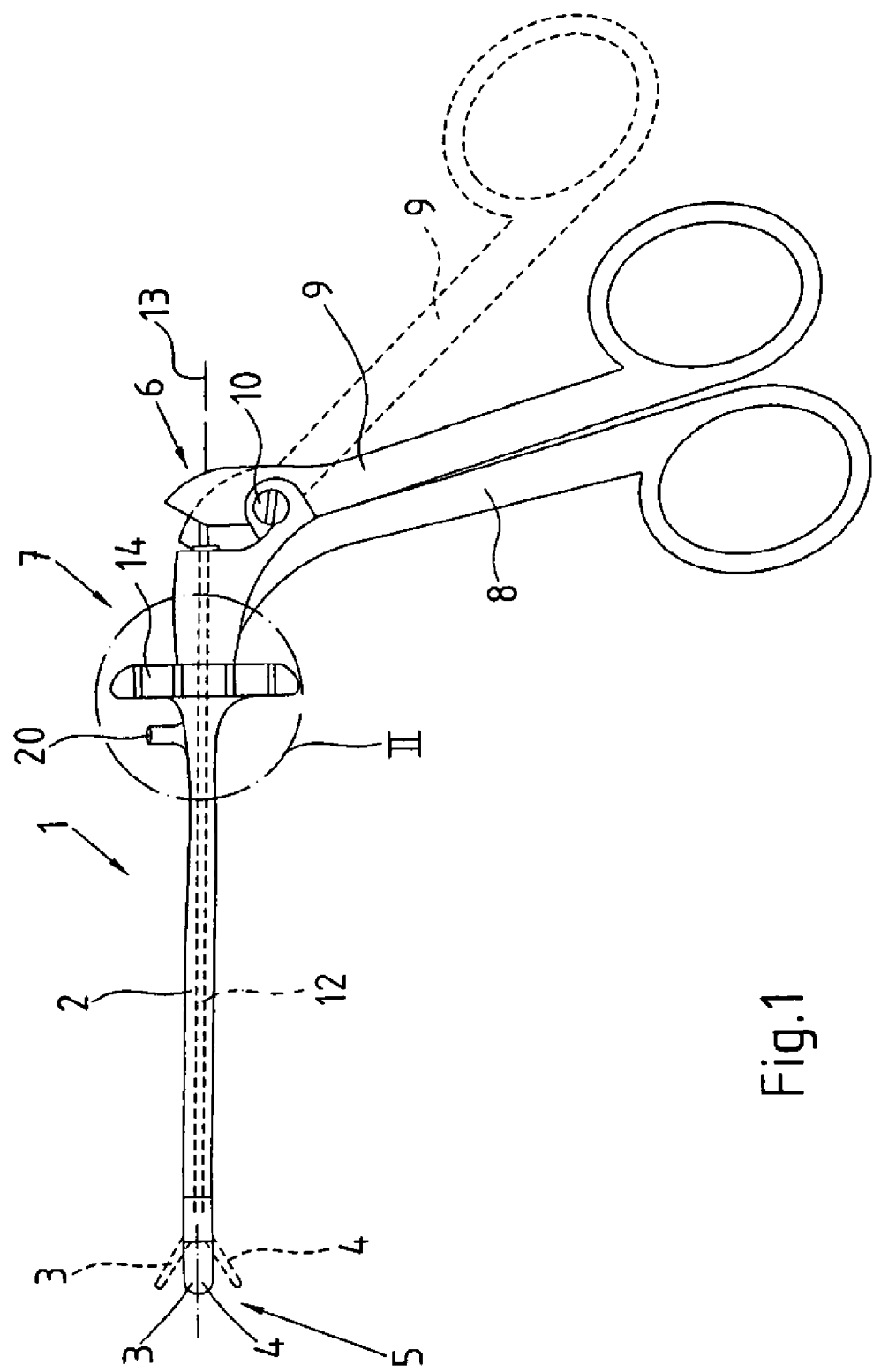
FIG. 1 shows a schematic side view of a first embodiment of a medical instrument according to the invention.
Figure 4:
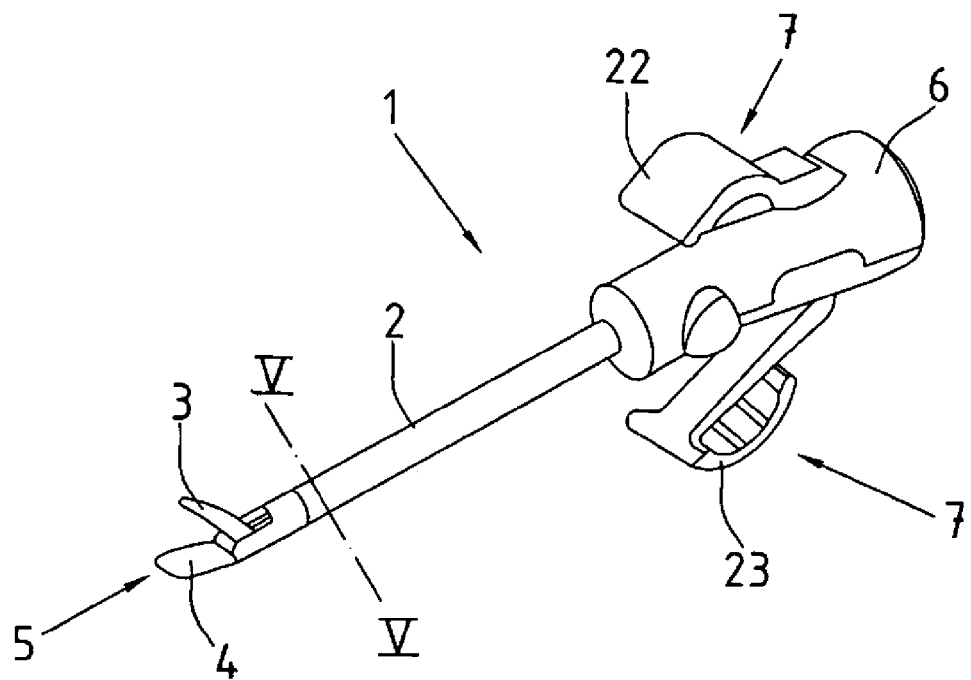
FIG. 4 shows a perspective view of a second embodiment of a medical instrument according to the invention.

The figures FIG. 1 and FIG. 4 show medical instruments 1, the force transmission mechanisms of which can be used for a variety of applications, such as, for example, for punches, scissors, needle holders, gripping instruments and the like.

The medical instruments 1 illustrated essentially consist of a hollow shank 2, at the distal end of which a tool 5 consisting of two pivotable jaw parts 3 and 4 is arranged, and at the proximal end of which a handle 6 is arranged, wherein the jaw parts 3 and 4 of the tool 5 are actuable via drives 7 arranged on the handle 6.

In the first embodiment, which is illustrated in FIG. 1, the handle 6 has two grip parts 8 and 9, wherein the grip part 8 is formed integrally and rigidly with the handle 6, and the other grip part 9 can be pivoted about a pivot axis 10 in relation to the rigid grip part 8. The pivotable grip part 9 forms the drive 7 for the upper jaw part 3 of the tool 5.

The pivotable grip part 9 and the upper jaw part 3 are operatively connected to each other via a push/pull element 11, which is designed as a push/pull rod 12 mounted in an axially displaceable manner in the hollow shank 2, in such a manner that, by pivoting of the grip part 9 of the handle 6, the upper jaw part 3 of the tool 5 can be transferred from the closed position (solid illustration according to FIG. 1) into the open position (dashed illustration according to FIG. 1) or vice versa. In FIG. 1, the respectively associated position of the pivotable grip part 9 of the handle 6 is likewise illustrated in solid form (for the closed position) and dashed form (for the open position).

Figure 2:
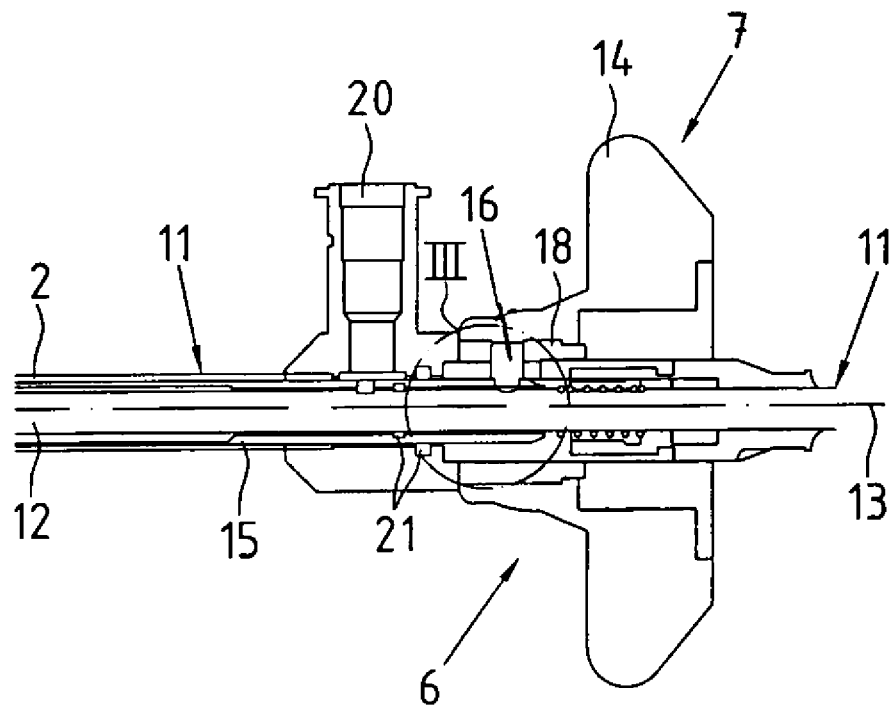
FIG. 2 shows an enlarged longitudinal section through the detail II according to FIG. 1.
Figure 3:
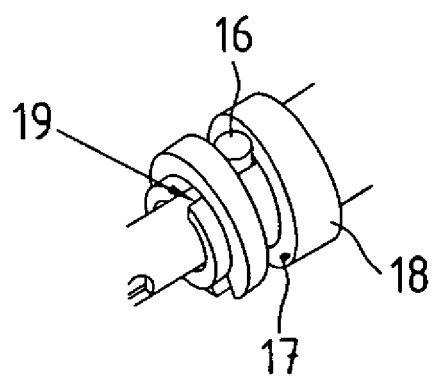
FIG. 3 shows a perspective view of the detail III according to FIG. 2.

In this embodiment, the drive 7 for the lower jaw part 4 is designed as an adjusting wheel 14 which is rotatable about the longitudinal axis 13 of the shank 2. In order to actuate the lower jaw part 4, the adjusting wheel 14 and the lower jaw part 4 are operatively connected to each other via a push/pull element 11 which is designed as a push/pull tube 15 coaxially surrounding the push/pull rod 12, as can be gathered from the figures FIGS. 2 and 3.

In order to convert the rotational movement of the adjusting wheel 14 into the axial movement of the push/pull tube 15, the push/pull tube 15 has a control pin 16 which is fixedly connected to the push/pull tube 15 and engages in a helical guide track 17 arranged in the adjusting wheel 14. In the embodiment 5 illustrated, the helical guide track 17 is arranged in a sleeve 18 which can be fixed in the adjusting wheel 14.

The adjusting wheel 14 and the lower jaw part 4 are operatively connected to each other via the push/pull tube 15, which coaxially surrounds the push/pull rod 12, in such a manner that, by rotation of the adjusting wheel 14 of the handle 6, the lower jaw part 4 of the tool 5 can be transferred from the closed position (solid illustrated according to FIG. 1) into the open position (dashed illustration according to FIG. 1), or vice versa.

By means of the rotation of the adjusting wheel 14 about the longitudinal axis 13 of the shank 2, the control pin 16, which is mounted in the helical guide track 17 is displaced inn the axial direction of the shank 2 distally or proximally, as a result of which the push/pull tube 15, which is fixedly connected to the control pin 16, is likewise displaced axially distally or proximally, this, for its part, causing the lower jaw part 4 to open or close. In order to prevent the push/pull tube 15 being transferred via the control pin 16 mounted in the guide track 17 into a rotational movement about the longitudinal axis 13 of the shank 2, the control pin 16 is mounted in a manner such that it is guided over the entire displacement path thereof in a longitudinal slot 19 formed in the handle 6, as can be gathered from FIG. 3.

In order to ensure that an insufflation gas or rinsing liquid which is supplied or removed via a suction/rinsing connection 20 cannot escape proximally via the push/pull elements 11 mounted in an axially displaceable manner in the shank 2, namely the push/pull rod 12 and the push/pull tube 15, the push/pull rod 12 and the push/pull tube 15 are mounted in a fluid-proof manner in the handle 6 via sealing elements 21, in particular O rings 21.

The two drives 7 which are actuable independently of each other, namely the pivotable grip part 9 and the adjusting wheel 14, permit separate pivoting in each case of the associated jaw parts 3 and 4 of the tool 5.

In the second embodiment, which is illustrated in FIG. 4, the handle 6 has two levers 22 and 23 which are mounted pivotably on the handle 6. The levers 22 and 23 form the drives 7 for the jaw parts 3 and 4 of the tool 5.

The levers 22 and 23 and the jaw parts 3 and 4 are operatively connected to each other via a respective push/pull element 11, which is designed as a push/pull rod 24 mounted in an axially displaceable manner in the hollow shank 2, in such a manner that, by pivoting of the levers 22, 23 of the handle 6, the jaw parts 3 and 4 of the tool 5 can be transferred from the closed position into the open position and vice versa.

In this second embodiment too, the two drives 7 which are designed as separate pivotable levers 22 and 23 each permit separate pivoting of the individual jaw parts 3 and 4 of the tool 5.

Figure 5:
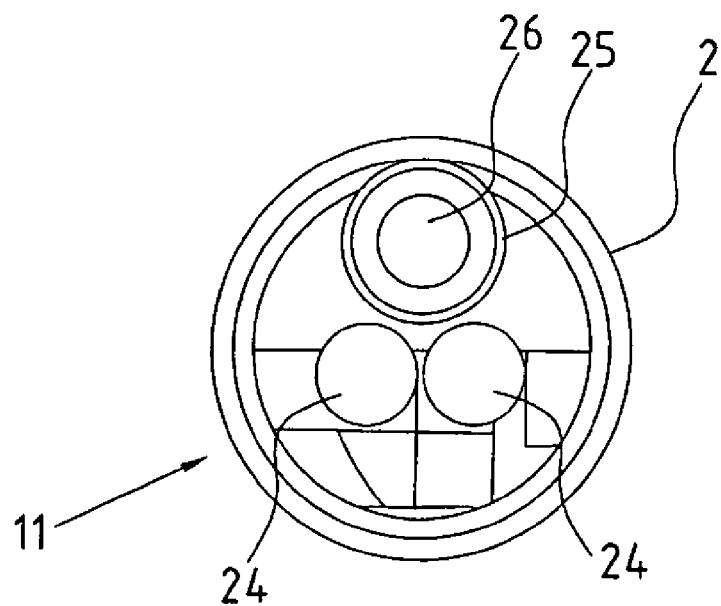
FIG. 5 shows an enlarged section along the line V-V according to FIG. 4.

As is apparent from FIG. 5, in the illustrated embodiment of the medical instrument 1, an empty tube 25 which extends as far as the tool 5 and is intended for receiving a medical instrument or a medical aid, such as, for example, a catheter 26, is additionally arranged in the shank 2 and in the handle 6.

What is claimed is:

1. A medical instrument comprising:
    a tool with two pivotable jaw parts arranged on the distal end of a shank and a handle arranged on the proximal end of the shank;
    wherein the two pivotable jaw parts of the tool can be pivoted relative to each other independently of each other via the handle and each of the two pivotable jaw parts can be actuated via a separate drive arranged on the handle;
    wherein one drive is designed as a grip part which is mounted pivotably on the handle and is operatively connected to one jaw part of the tool via a first push/pull element mounted in an axially displaceable manner in the shank; and
    another drive is designed as an adjusting wheel which is rotatable about a longitudinal axis of the shank and is operatively connected to the other jaw part of the tool via a second push/pull element mounted in an axially displaceable manner in the shank, characterized in that
    the first push/pull element which is coupled to the pivotable grip part is designed as an axially displaceable push/pull rod, and in that the second push/pull element which is coupled to the adjusting wheel is designed as an axially displaceable hollow push/pull tube coaxially surrounding the push/pull rod, wherein the push/pull rod is arranged inside the hollow push/pull tube.

2. The medical instrument according to claim 1, characterized in that the jaw parts of the tool can be bent in relation to the longitudinal axis of the instrument.

3. The medical instrument according to claim 1, characterized in that the push/pull rod and the push/pull tube are mounted in a fluid-proof manner in the handle via sealing elements.

4. The medical instrument according to claim 3, characterized in that the rotational movement of the adjusting wheel can be converted via a helical guide track and a control pin engaging in the guide track into an axial movement of the push/pull tube.

5. The medical instrument according to claim 4, characterized in that the control pin is fixedly connected to the push/pull tube, and the helical guide track is formed in the adjusting wheel.

6. The medical instrument according to claim 5, characterized in that the control pin is mounted in a manner such that it is guided in a longitudinal slot formed in the handle.

7. The medical instrument according to claim 1, characterized in that each of the drives is designed as levers which are mounted pivotably on the handle, each lever being operatively connected to a respective jaw part of the tool via a respective push/pull element.

8. The medical instrument according to claim 7, characterized in that the two push/pull elements are designed as push/pull rods which are mounted in an axially displaceable manner parallel to each other in the shank.

9. The medical instrument according to claim 1, characterized in that an empty tube which extends as far as the tool and receives a medical instrument or medical aid is additionally arranged in the shank and in the handle.

\* \* \* \* \*